(12) United States Patent
Ostrow

(10) Patent No.: US 7,970,468 B1
(45) Date of Patent: Jun. 28, 2011

(54) METHOD FOR PROGRAMMING ARRHYTHMIA DISCRIMINATION ALGORITHMS IN ICDS

(75) Inventor: Eliot L. Ostrow, Sunnyvale, CA (US)

(73) Assignee: Pacesetter, Inc., Sunnyvale, CA (US)

( * ) Notice: Subject to any disclaimer, the term of this patent is extended or adjusted under 35 U.S.C. 154(b) by 1146 days.

(21) Appl. No.: 11/683,503

(22) Filed: Mar. 8, 2007

(51) Int. Cl.
*A61N 1/08* (2006.01)

(52) U.S. Cl. .......................................... 607/14; 600/518

(58) Field of Classification Search .................. 607/14; 600/518
See application file for complete search history.

(56) References Cited

U.S. PATENT DOCUMENTS

| | | | |
|---|---|---|---|
| 6,636,764 B1 | 10/2003 | Fain et al. | |
| 6,922,584 B2 | 7/2005 | Wang et al. | |
| 6,959,212 B2 | 10/2005 | Hsu et al. | |
| 7,031,764 B2 | 4/2006 | Schwartz et al. | |
| 7,076,300 B1 | 7/2006 | Kroll et al. | |
| 7,092,761 B1 | 8/2006 | Cappa et al. | |
| 7,120,491 B1 | 10/2006 | Bailin et al. | |
| 7,139,607 B1 | 11/2006 | Shelchuk | |
| 2004/0059395 A1* | 3/2004 | North et al. | 607/48 |
| 2007/0197928 A1* | 8/2007 | Kim et al. | 600/515 |

* cited by examiner

*Primary Examiner* — Eric D. Bertram
(74) *Attorney, Agent, or Firm* — Theresa Takeuchi; Steven M. Mitchell

(57) ABSTRACT

Embodiments of the present invention are for use with implantable cardiac devices that have discriminator parameters that the devices use to discriminate between ventricular tachycardia (VT) and supraventricular tachyarrhythmia (SVT). A user is allowed to select a balance setting that specifies a balance between sensitivity and specificity, where an increase in sensitivity results in a decrease in specificity, and vice versa. In response to the user selecting the balance setting, a value of at least one of the discriminator parameters and/or how at least one of the discriminator parameters is used is automatically adjusted. The more the balance setting favors sensitivity, then the more likely an actual VT will be characterized as VT, but the more likely an actual SVT may be characterized as VT. The more the balance setting favors specificity, then the less likely an actual SVT will characterized as VT, but the less likely an actual VT may be characterizes as VT.

20 Claims, 6 Drawing Sheets

--- allow a user to select a balance setting that specifies a balance between sensitivity and specificity, wherein an increase in sensitivity results in a decrease in specificity, and vice versa — 402 automatically adjust a value of at least one of the discriminator parameters and/or how at least one of the discriminator parameters is used, in response to the user selecting the balance setting — 404

METHOD FOR PROGRAMMING ARRHYTHMIA DISCRIMINATION ALGORITHMS IN ICDS

FIELD OF THE INVENTION

Embodiments of the present invention relate to implantable cardiac devices, and methods for use therewith, that are used to discriminate between different types of arrhythmias.

BACKGROUND

In a normal heart, cells of the sinoatrial node (SA node) spontaneously depolarize and thereby initiate an action potential. This action potential propagates rapidly through the atria (which contract), slowly through the atrioventricular node (AV node), the atriventricular bundle (AV bundle or His bundle) and then to the ventricles, which causes ventricular contraction. This sequence of events is known as normal sinus rhythm (NSR). Thus, in a normal heart, ventricular rhythm relies on conduction of action potentials through the AV node and AV bundle.

Rhythms that do not follow the sequence of events described above are known as arrhythmias. Those that result in a heart rate slower than normal are known as bradyarrhythmias; those that result in a faster heart rate than normal are called tachyarrhythmias. Tachyarrhythmias are further classified as supraventricular tachyarrhythmias and ventricular tachyarrhythmia. Supraventricular tachyarrhythmias (SVTs) are characterized by abnormal rhythms that may arise in the atria or the atrioventricular node (AV node). For example, a paroxysmal SVT can exhibit heart rates between approximately 140 beats per minute (bpm) and approximately 250 bpm. However, the most common SVTs are typically atrial flutter (AFl) and atrial fibrillation (AF). In addition, many SVTs involve the AV node, for example, AV nodal reentry tachycardia (AVNRT) where an electrical loop or circuit includes the AV node.

Atrial flutter (AFl) can result when an early beat triggers a "circus circular current" that travels in regular cycles around the atrium, pushing the atrial rate up to approximately 250 bpm to approximately 350 bpm. The atrioventricular node between the atria and ventricles will often block one of every two beats, keeping the ventricular rate at about 125 bpm to about 175 bpm. This is the pulse rate that will be felt, even though the atria are beating more rapidly. At this pace, the ventricles will usually continue to pump blood relatively effectively for many hours or even days. A patient with underlying heart disease, however, may experience chest pain, faintness, or even heart failure as a result of the continuing increased stress on the heart muscle. In some individuals, the ventricular rate may also be slower if there is increased block of impulses in the AV node, or faster if there is little or no block.

If the cardiac impulse fails to follow a regular circuit and divides along multiple pathways, a chaos of uncoordinated beats results, producing atrial fibrillation (AF). AF commonly occurs when the atrium is enlarged (usually because of heart disease). In addition, it can occur in the absence of any apparent heart disease. In AF, the atrial rate can increase to more than 350 bpm and cause the atria to fail to pump blood effectively. Under such circumstances, the ventricular beat may also become haphazard, producing a rapid irregular pulse. Although AF may cause the heart to lose approximately 20 to 30 percent of its pumping effectiveness, the volume of blood pumped by the ventricles usually remains within the margin of safety, again because the atrioventricular node blocks out many of the chaotic beats. Hence, during AF, the ventricles may contract at a lesser rate than the atria, for example, of approximately 125 bpm to approximately 175 bpm.

Overall, SVTs are not typically immediately life threatening when compared to ventricular arrhythmias, examples of which are discussed below.

Ventricular arrhythmias, which originate in the ventricles, include ventricular tachycardia (VT) and ventricular fibrillation (VF). Ventricular arrhythmias are often associated with rapid and/or chaotic ventricular rhythms. For example, sustained ventricular tachycardia can lead to ventricular fibrillation. In sustained ventricular tachycardia, consecutive impulses arise from the ventricles at a rate of 100 bpm or more. Such activity may degenerate further into disorganized electrical activity known as ventricular fibrillation (VF). In VF, disorganized action potentials can cause the myocardium to quiver rather than contract. Such chaotic quivering can greatly reduce the heart's pumping ability. Indeed, approximately two-thirds of all deaths from arrhythmia are caused by VF. A variety of conditions such as, but not limited to, hypoxia, ischemia, pharmacologic therapy (e.g., sympathomimetics), and asynchronous pacing may promote onset of ventricular arrhythmia.

It has been common practice for an implantable cardioverter defibrillator (ICD) to monitor heart rate, or more commonly the ventricular rate, of a patient and classify the cardiac condition of the patient based on this heart rate. For example, a tachyarrhythmia may be defined as any rate in a range above a designated threshold. This range is then divided into ventricular tachycardia and ventricular fibrillation zones. The ventricular tachycardia zone may be further divided into slow ventricular tachycardia and fast ventricular tachycardia zones.

As described above, SVTs and ventricular arrhythmias may lead to ventricular rates in excess of 100 bpm. In other words, ventricular rates of SVTs can overlap with rates of tachycardias of ventricular origin. These SVTs are often well tolerated and require no intervention. Further, physically active patients can have heart rates during exercise that overlap with their tachycardia rates. Accordingly, discrimination of VT from SVT, including increased heart rates due to exercise, may require more than just knowledge of a patient's ventricular rate. In other words, using heart rate as the sole criterion to classify the cardiac condition of a patient is often not sufficient.

To improve the specificity and accuracy of arrhythmia characterization, many implantable cardiac devices (ICDs) can also examine the morphology of an intracardiac electrogram (IEGM), in addition to the heart rate. The shape of an intracardiac complex can include information on the origin and sequence of the heart's electrical activity. A normal intracardiac complex traverses the AV node and is conducted by specialized cardiac tissue throughout the ventricles. This results in a distinctive complex morphology. A tachycardia of ventricular origin often has a different morphology due to its ectopic origin and conductance through cardiac muscle tissue. As such, in addition to monitoring heart rate, some ICDs are capable of performing morphology discrimination to classify the cardiac condition of the patient. For example, a template based on the morphology of a "known" signal can be stored in the ICD. The "known" signal can be, for example, a signal collected during a period where a patient is known to exhibit a normal sinus rhythm. By comparing the morphology characteristics (e.g., number, amplitude, sequence and/or polarity of waveform peaks, as well as the area of the peaks) of an arrhythmia to the template, the ICD can calculate the match (or lack thereof) between the waveforms. For a further description of morphology discrimination, refer to U.S. Pat. No. 5,240,009 (Williams), entitled "Medical Device with Morphology Discrimination" and to U.S. Pat. No. 5,779,645 (Olson et al.), entitled "System and Method for Waveform Morphology Comparison," which patents are hereby incorporated by reference. These are just a few example of morphology discriminator algorithms and parameters, which are not intended to be limiting.

Sudden onset and interval stability (also know as rate stability), which are discussed in more detail below, are examples of other factors that can be monitored to improve the specificity of arrhythmia characterization. Also, the relationship between ventricular rate (V) and atrial rate (A) can be used to characterize an arrhythmia. For example, this can be part of a rate branch algorithm, which, depending on V and A, may follow one of three branches: a V<A rate branch; a V=A (within a specified tolerance) rate branch; and a V>A rate branch. If V<A, then morphology discrimination and/or interval stability may be available to distinguish VT from AF or AFl. If A and V are essentially the same (within a certain tolerance), then morphology discrimination and/or sudden onset may be available to distinguish VT from sinus tachycardia. If V>A, then an arrhythmia may be characterized as VT. Also, specific branches can be turned on or off. For example, if V is greater than the tachycardia threshold but essentially the same as A, and the V=A branch is turned off, then the algorithm can cause the V>A branch to be followed, and the arrhythmia may be classified as VT. Additional details of an exemplary rate branch algorithm are provided in U.S. Pat. No. 6,636,746 (Fain et al.), entitled "Safety Backup in Arrhythmia Discrimination Algorithm," which is incorporated herein by reference. Also, atrioventricular association (AVA) can also be used to AFl from VT. In an exemplary (AVA) algorithm, the AV interval is measured from each ventricular sensed event to its preceding atrial event and an AVA Delta is then calculated as the difference between the second longest AV interval and the second shortest AV interval in a recent group of intervals. If the measured AVA Delta is less than a programmable AVA threshold parameter, the AV intervals are considered stable, which is indicative of SVT. If the measured AVA Delta is greater than or equal to a programmable AVA threshold parameter, the AV intervals are considered unstable, which is indicative of VT. More generally, the relative rate of the atria and ventricles and/or the timing relationship between atrial and ventricular events can be considered.

Typically an ICD is programmed to provide a therapy in response to an arrhythmia being detected, where the type of therapy corresponds to the type of arrhythmia that the ICD believes it has detected. For example, VT may be treated with a therapy consisting of low-energy pacing pulses designed to capture the ventricles. This therapy is referred to as Anti-Tachycardia Pacing therapy (ATP). VT may also be treated with relatively low energy, synchronized cardioversion shocks. VF, on the other hand, is typically treated more aggressively with high energy shocks. The ICD is programmed with numerous parameters that are used to discriminate between types of arrhythmias, and to define the types of therapies to be used to treat the various arrhythmias. An SVT may or may not be treated, depending on how an ICD is programmed.

Over the years, the number of programmable parameters has been increasing steadily. A modern ICD may have up to 200 or more programmable parameters. A major challenge for both ICD manufacturer and caregivers (e.g., physicians, clinician, or the like) is to select proper values and uses of these parameters. While the manufacturer may provide nominal values and uses of these parameters (also referred to as default parameters and criteria), these nominal values and uses may not be proper for all patients and it is up to the caregiver to change them using statistical information, knowledge of the patient and his/her condition, and the caregiver's personal experience.

Caregivers often have difficulty programming ICD parameters intended to aid in the discrimination of SVT from VT, because the implications of making adjustments to them are not clear. As a result, caregivers often either do not turn on these discriminators routinely, waiting to see if the patient will receive inappropriate therapies before attempting to program the device appropriately, or they turn the discriminators on with the default parameters provided by the manufacturer, without any attempt to customize them for the individual needs of the patient.

Historically, ICD manufacturers developed default criteria for discriminators based on the fact that the initial indications for ICD implantation included documented lethal arrhythmias or survival of an episode of sudden cardiac death. Given those indications, the defaults were chosen based on the fact that a single episode of an arrhythmia could be lethal, and therefore adhered to the philosophy that "it's better to give ten shocks too many than one too few." In general, because these so-called "secondary prevention" patients had already survived a potentially lethal arrhythmia, they were somewhat willing to accept an inappropriate shock, because they understood the consequences of not receiving a shock when actually needed. In addition, since these patients already had documented arrhythmias and/or had undergone electrophysiology studies, the types of arrhythmias they had (e.g., VT vs. primary VF), and their hemodynamic tolerance of those arrhythmias, was often known.

Today, the ICD implant population, and the indications for implantation have changed, such that a large percentage of patients receiving ICDs or other tachyarrhythmia control devices are so-called "primary prevention" patients, i.e., those who are at risk for tachyarrhythmias and sudden cardiac death, but who have not yet shown any evidence of actually having experienced such arrhythmias. For these patients, their understanding of their need for an ICD is often much less clear, and they are, therefore, much less tolerant of inappropriate shocks from a device that they are not convinced that they need. Moreover, since these patients have not experienced arrhythmias nor undergone electrophysiology studies, the type and tolerance of arrhythmias they may experience in the future is largely unknown.

Despite the shift in patient populations, manufacturers of ICDs and other arrhythmia control devices have been reluctant to change the default values for the discriminators to something "less safe", because not all patients fall into the primary prevention category. Coupled with caregivers' reluctance to program away from those default values because the implications/risks of doing so are unclear, the result is that the proper weighing of discrimination sensitivity vs. specificity is often not addressed by caregivers until the patient has received inappropriate therapies.

Accordingly, there is still a need to assist physicians, clinicians and other caregivers in programming discrimination algorithms in a way more appropriate to the indications and characteristics of patients.

SUMMARY

Embodiments of the present invention are directed to methods for use with implantable cardiac devices that have discriminator parameters that the devices use to discriminate between ventricular tachycardia (VT) and supraventricular tachyarrhythmia (SVT). Embodiments of the present invention are also directed to implantable cardiac devices, as well as external programmers, that are configured to implement such methods.

In accordance with an embodiment of the present invention, a user (e.g., caregiver) is allowed to select a balance setting that specifies a balance between sensitivity and specificity, where an increase in sensitivity results in a decrease in specificity, and vice versa. Thereafter, in response to the user selecting the balance setting, a value of at least one of the discriminator parameters and/or how at least one of the discriminator parameters is used is automatically adjusted. The more the balance setting favors sensitivity, then the more likely an actual VT will be characterized as VT, but the more likely an actual SVT may be characterized as VT. The more the balance setting favors specificity, then the less likely an actual SVT will characterized as VT, but the less likely an actual VT may be characterizes as VT. Exemplary discriminator parameters include, but are not limited to, a tachycardia detection rate parameter, an interval stability parameter, an atrioventricular association parameter, a sudden onset parameter and a morphology parameter.

The user can be allowed to select the balance setting by presenting the user with at least two different options (each of which corresponds to a different balance setting), and allowing the user to select one of the options. The at least two different options can include a first option and a second option, where the first option corresponds to a first sensitivity and first specificity, and the second option corresponds to a second sensitivity and a second specificity (where the first sensitivity is greater than the second sensitivity, and the first specificity is less than the second specificity). In a specific embodiment, such a first option can be presented to the user as a "secondary prevention" option for use with secondary prevention patients, and the second option can be presented to the user as a "primary prevention" option for use with primary prevention patients.

In specific embodiments, the user can be presented with the at least two different options via an external programmer that is configured to wirelessly communicate with the implantable cardiac stimulation device. In such embodiments, the user can select one of the at least two different options, using a user interface of the programmer.

In accordance with certain embodiments, the user is presented with a sliding scale bar having a first end and a second end, where the first end corresponds to a first sensitivity and first specificity, and the second end corresponds to a second sensitivity and a second specificity (where the first sensitivity is greater than the second sensitivity, and the first specificity is less than the second specificity). In such embodiments, the user can select a position on the scale between, and inclusive of, the first and second ends, with the selected position corresponding to the balance setting selected by the user.

The automatic adjustment can include adjusting a value of one or more of the discriminator parameters, in response to the user selecting the balance setting. Alternatively, or additionally, the automatic adjustment can include adjusting how many discriminator criteria must be satisfied for a rhythm to be characterized as VT (where at least some of the discriminator criteria are specified at least in part by a corresponding one of the discriminator parameters). Alternatively, or additionally, the automatic adjustment can include adjusting which discriminator criteria are turned on, which can specify which discriminator parameters are used.

This summary is not intended to be a complete description of the invention. Other features and advantages of the invention will appear from the following description in which the preferred embodiments have been set forth in detail, in conjunction with the accompanying drawings and claims.

DETAILED DESCRIPTION OF PREFERRED EMBODIMENTS

The following description includes a best mode presently contemplated for the device. This description is not to be taken in a limiting sense but is made merely for the purpose of describing the general principles of the device. In the description that follows, like numerals or reference designators will be used to refer to like parts or elements throughout.

The disclosed systems and methods, which are for use in discriminating between different types of arrhythmias, are generally intended for use with an implantable cardiac device capable of detecting and treating arrhythmias. An exemplary implantable cardiac device will thus be described in conjunction with FIGS. 1 and 2, in which embodiments of the present invention described herein could be implemented. Additionally, FIGS. 3A and 3B will be used to described an exemplary external programmer that can be used to program implantable cardiac devices, as well as upload information from implantable cardiac devices and analyze such information. It is recognized, however, that numerous variations of such a device exist in which the methods could be implemented.

Exemplary Implantable Cardiac Stimulation Device

Figure 1:
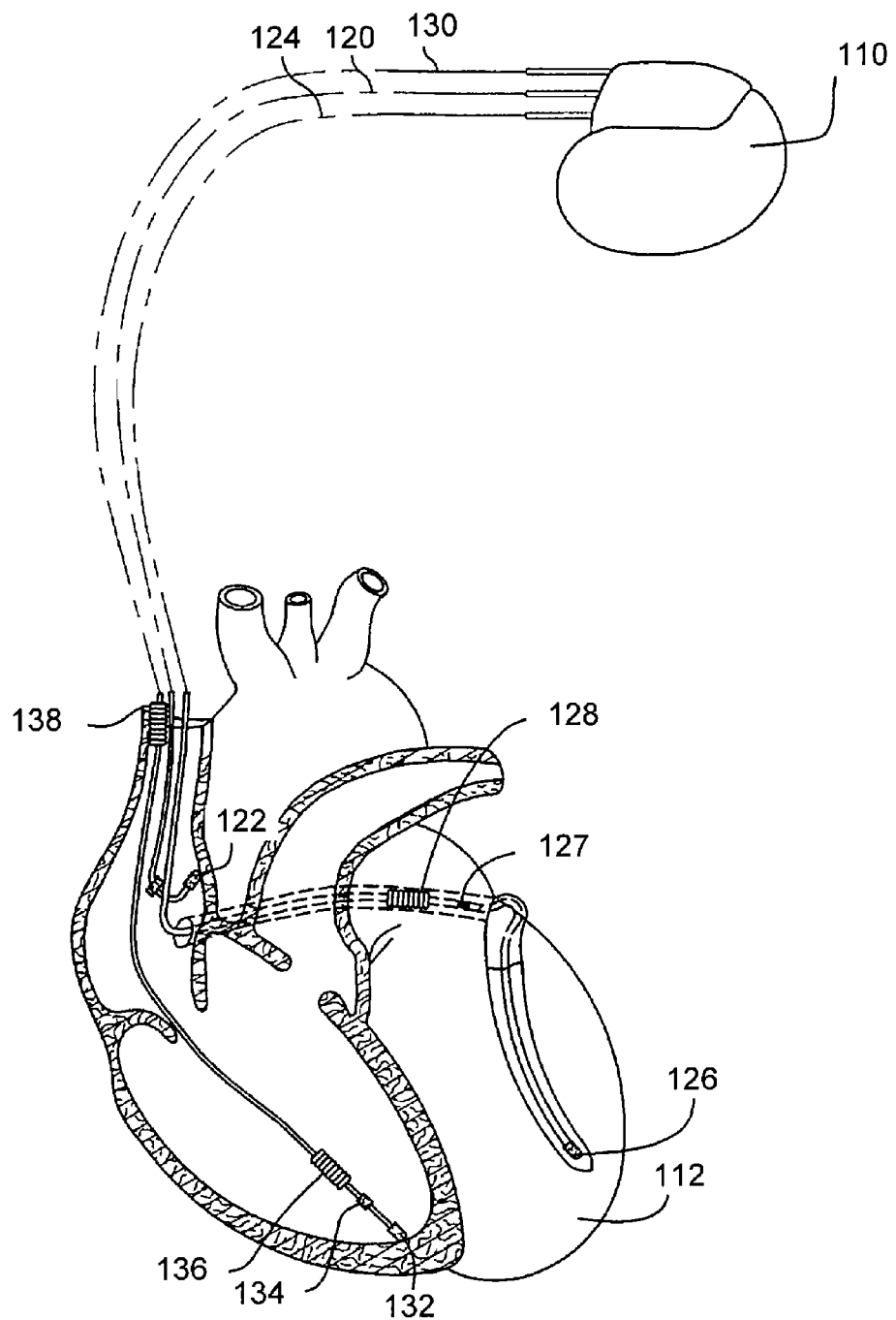
FIG. 1 is a simplified, partly cutaway view illustrating an implantable stimulation device in electrical communication with at least three leads implanted into a patient's heart for delivering multi-chamber stimulation and shock therapy.

Referring to FIG. 1, an exemplary implantable device 110 (also referred to as a pacing device, a pacing apparatus, a cardiac stimulation device, or simply a device) is in electrical communication with a patient's heart 112 by way of three leads, 120, 124 and 130, suitable for delivering multi-chamber stimulation. Preferably, the exemplary device 110 is also capable of delivering shock therapy.

To sense atrial cardiac signals and to provide right atrial chamber stimulation therapy, the stimulation device 110 is coupled to an implantable right atrial lead 120 having at least an atrial tip electrode 122, which typically is implanted in the patient's right atrial appendage. To sense left atrial and ventricular cardiac signals and to provide left-chamber pacing therapy, the stimulation device 110 is coupled to a "coronary sinus" lead 124 designed for placement in the "coronary sinus region" via the coronary sinus for positioning a distal electrode adjacent to the left ventricle and/or additional electrode(s) adjacent to the left atrium. As used herein, the phrase "coronary sinus region" refers to the vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus.

Accordingly, an exemplary coronary sinus lead 124 is designed to receive left atrial and ventricular cardiac signals and to deliver left atrial and ventricular pacing therapy using at least a left ventricular tip electrode 126, left atrial pacing therapy using at least a left atrial ring electrode 127, and shocking therapy using at least a left atrial coil electrode 128. The present invention may of course be practiced with a coronary sinus lead that does not include left atrial sensing, pacing or shocking electrodes.

The stimulation device 110 is also shown in electrical communication with the patient's heart 112 by way of an implantable right ventricular lead 130 having, in this embodiment, a right ventricular tip electrode 132, a right ventricular ring electrode 134, a right ventricular (RV) coil electrode 136, and an SVC coil electrode 138. Typically, the right ventricular lead 130 is transvenously inserted into the heart 112 so as to place the right ventricular tip electrode 132 in the right ventricular apex so that the RV coil electrode 136 will be positioned in the right ventricle and the SVC coil electrode 138 will be positioned in the superior vena cava. Accordingly, the right ventricular lead 130 is capable of receiving cardiac signals and delivering stimulation in the form of pacing and shock therapy to the right ventricle. It will be understood by those skilled in the art that other lead and electrode configurations such as epicardial leads and electrodes may be used in practicing the invention.

Figure 2:
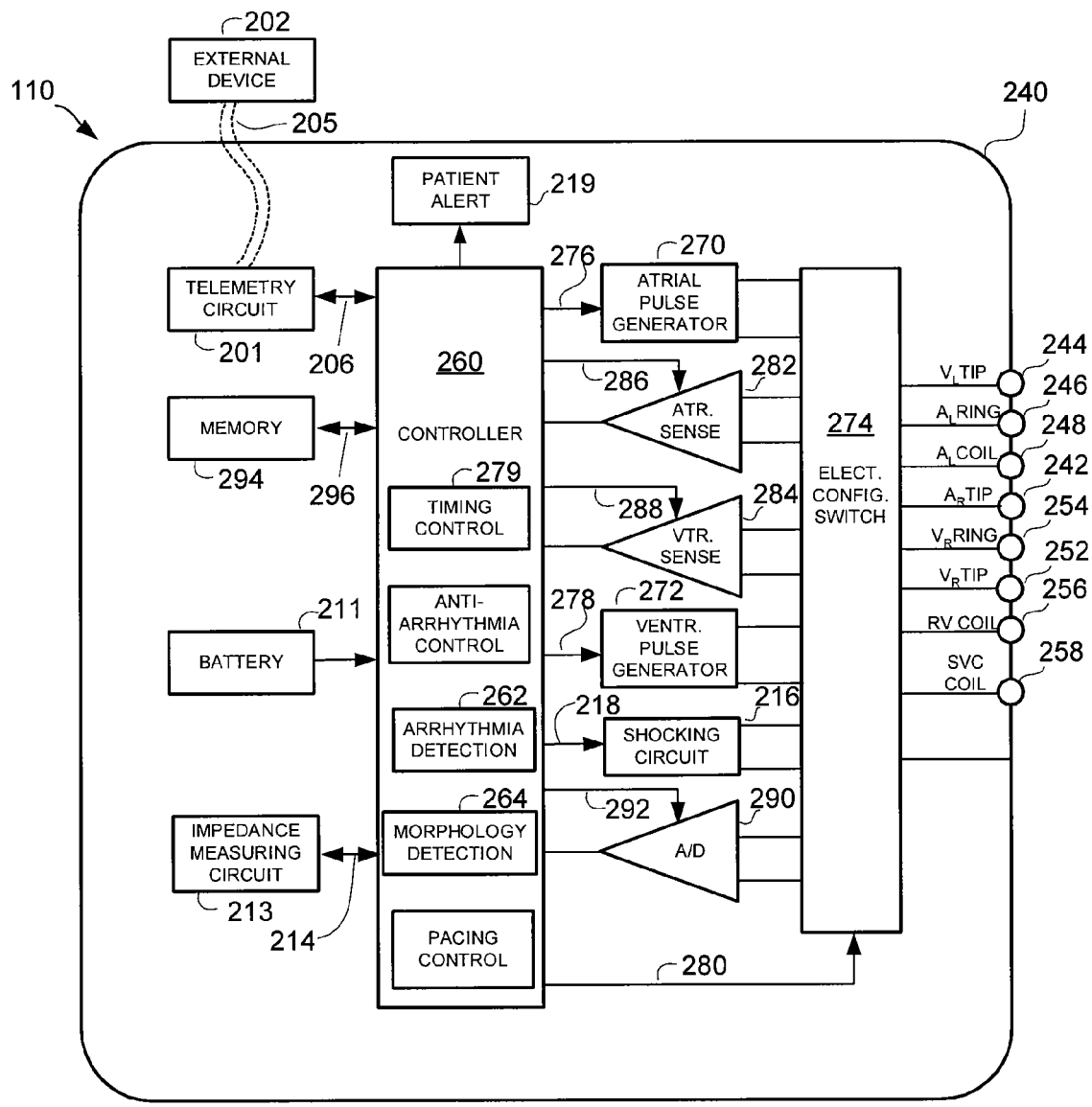
FIG. 2 is a functional block diagram of the multi-chamber implantable stimulation device of FIG. 1, illustrating the basic elements that provide pacing stimulation, cardioversion, and defibrillation in four chambers of the heart.

As illustrated in FIG. 2, a simplified block diagram is shown of the multi-chamber implantable implantable device 110, which is capable of treating both fast and slow arrhythmias with stimulation therapy, including pacing, cardioversion and defibrillation stimulation. While a particular multi-chamber device is shown, this is for illustration purposes only, and one of skill in the art could readily duplicate, eliminate or disable the appropriate circuitry in any desired combination to provide a device capable of treating the appropriate chamber(s) with pacing, cardioversion and defibrillation stimulation.

The housing 240 for the implantable device 110, shown schematically in FIG. 2, is often referred to as the "can", "case" or "case electrode" and may be programmably selected to act as the return electrode for all "unipolar" modes. The housing 240 may further be used as a return electrode alone or in combination with one or more of the coil electrodes, 128, 136 and 138, for shocking purposes. The housing 240 further includes a connector (not shown) having a plurality of terminals, 242, 244, 246, 248, 252, 254, 256, and 258 (shown schematically and, for convenience, the names of the electrodes to which they are connected are shown next to the terminals). As such, to achieve right atrial sensing and pacing, the connector includes at least a right atrial tip terminal ($A_R$ TIP) 242 adapted for connection to the atrial tip electrode 122.

To achieve left atrial and ventricular sensing, pacing and shocking, the connector includes at least a left ventricular tip terminal ($V_L$ TIP) 244, a left atrial ring terminal ($A_L$ RING) 246, and a left atrial shocking terminal ($A_L$ COIL) 148, which are adapted for connection to the left ventricular ring electrode 126, the left atrial tip electrode 127, and the left atrial coil electrode 128, respectively.

To support right ventricle sensing, pacing and shocking, the connector further includes a right ventricular tip terminal ($V_R$ TIP) 252, a right ventricular ring terminal ($V_R$ RING) 254, a right ventricular shocking terminal (Rv COIL) 256, and an SVC shocking terminal (SVC COIL) 258, which are adapted for connection to the right ventricular tip electrode 132, right ventricular ring electrode 134, the RV coil electrode 136, and the SVC coil electrode 138, respectively.

At the core of the implantable device 110 is a programmable microcontroller 260 which controls the various types and modes of stimulation therapy. As is well known in the art, the microcontroller 260 typically includes a microprocessor, or equivalent control circuitry, designed specifically for controlling the delivery of stimulation therapy and can further include RAM or ROM memory, logic and timing circuitry, state machine circuitry, and I/O circuitry. Typically, the microcontroller 260 includes the ability to process or monitor input signals (data) as controlled by a program code stored in a designated block of memory. The details of the design of the microcontroller 260 are not critical to the present invention. Rather, any suitable microcontroller 260 can be used to carry out the functions described herein. The use of microprocessor-based control circuits for performing timing and data analysis functions are well known in the art. In specific embodiments of the present invention, the microcontroller 260 performs some or all of the steps associated with arrhythmia detection and myocardial ischemia detection.

Representative types of control circuitry that may be used with the invention include the microprocessor-based control system of U.S. Pat. No. 4,940,052 (Mann et. al.) and the state-machines of U.S. Pat. No. 4,712,555 (Sholder) and U.S. Pat. No. 4,944,298 (Sholder). For a more detailed description of the various timing intervals used within the pacing device and their inter-relationship, see U.S. Pat. No. 4,788,980 (Mann et. al.). The '052, '555, '298 and '980 patents are incorporated herein by reference.

An atrial pulse generator 270 and a ventricular pulse generator 272 generate pacing stimulation pulses for delivery by the right atrial lead 120, the right ventricular lead 130, and/or the coronary sinus lead 124 via an electrode configuration switch 274. It is understood that in order to provide stimulation therapy in each of the four chambers of the heart, the atrial and ventricular pulse generators, 270 and 272, may include dedicated, independent pulse generators, multiplexed pulse generators, or shared pulse generators. The pulse generators, 270 and 272, are controlled by the microcontroller 260 via appropriate control signals, 276 and 278, respectively, to trigger or inhibit the stimulation pulses.

The microcontroller 260 further includes timing control circuitry 279 which is used to control pacing parameters (e.g., the timing of stimulation pulses) as well as to keep track of the timing of refractory periods, noise detection windows, evoked response windows, alert intervals, marker channel timing, etc., which is well known in the art. Examples of pacing parameters include, but are not limited to, atrio-ventricular delay, interventricular delay and interatrial delay.

The switch bank 274 includes a plurality of switches for connecting the desired electrodes to the appropriate I/O circuits, thereby providing complete electrode programmability. Accordingly, the switch 274, in response to a control signal 280 from the microcontroller 260, determines the polarity of the stimulation pulses (e.g., unipolar, bipolar, etc.) by selectively closing the appropriate combination of switches (not shown) as is known in the art.

Atrial sensing circuits 282 and ventricular sensing circuits 284 may also be selectively coupled to the right atrial lead 120, coronary sinus lead 124, and the right ventricular lead 130, through the switch 274 for detecting the presence of cardiac activity in each of the four chambers of the heart. Accordingly, the atrial (ATR. SENSE) and ventricular (VTR. SENSE) sensing circuits, 282 and 284, may include dedicated sense amplifiers, multiplexed amplifiers, or shared amplifiers. The switch 274 determines the "sensing polarity" of the cardiac signal by selectively closing the appropriate switches, as is also known in the art. In this way, the clinician may program the sensing polarity independent of the stimulation polarity.

Each sensing circuit, 282 and 284, preferably employs one or more low power, precision amplifiers with programmable gain and/or automatic gain control, bandpass filtering, and a threshold detection circuit, as known in the art, to selectively sense the cardiac signal of interest. The automatic gain control enables the device 110 to deal effectively with the difficult problem of sensing the low amplitude signal characteristics of atrial or ventricular fibrillation. Such sensing circuits, 282 and 284, can be used to determine cardiac performance values used in the present invention. Alternatively, an automatic sensitivity control circuit may be used to effectively deal with signals of varying amplitude.

The outputs of the atrial and ventricular sensing circuits, 282 and 284, are connected to the microcontroller 260 which, in turn, are able to trigger or inhibit the atrial and ventricular pulse generators, 270 and 272, respectively, in a demand fashion in response to the absence or presence of cardiac activity, in the appropriate chambers of the heart. The sensing circuits, 282 and 284, in turn, receive control signals over signal lines, 286 and 288, from the microcontroller 260 for purposes of measuring cardiac performance at appropriate times, and for controlling the gain, threshold, polarization charge removal circuitry (not shown), and timing of any blocking circuitry (not shown) coupled to the inputs of the sensing circuits, 282 and 286.

For arrhythmia detection, the device 110 includes an arrhythmia detector 262 and a morphology detector 264, that utilizes the atrial and ventricular sensing circuits, 282 and 284, to sense cardiac signals to determine whether a rhythm is physiologic or pathologic. The morphology detector 264 can, e.g., assess characteristics such as amplitude, area under curves, polarity, and shape, of detected cardiac rhythms.

The arrhythmia detector 264 can analyze the timing intervals between sensed events (e.g., P-waves, R-waves, and depolarization signals associated with fibrillation) and compare them to predefined rate zone limits (e.g., bradycardia, normal, low rate VT, high rate VT, and fibrillation rate zones), and various other characteristics such as morphology (as determined by the morphology detector 264) and/or sudden onset, stability, physiologic sensors, etc., in order to classify an arrhythmia, and thus, determine the type of remedial therapy that is needed (e.g., bradycardia pacing, anti-tachycardia pacing, cardioversion shocks or defibrillation shocks).

The arrhythmia detector 262 and/or morphology detector 264 can be implemented within the microcontroller 260, as shown in FIG. 2. Thus, the detectors 262 and/or 264 can be implemented by software, firmware, or combinations thereof. It is also possible that all, or portions, of the arrhythmia detector 262 and/or morphology detector 264 can be implemented using hardware. Further, it is also possible that all, or portions, of the detectors 262 and/or 264 can be implemented separate from the microcontroller 260. It is also possible that the features of the arrhythmia detector and morphology detector be incorporated into a single detector. These detectors can use discriminator parameters to assist in classifying arrhythmias. Values and uses of such parameters can be automatically adjusted in accordance with embodiments of the present invention, as described below.

Exemplary types of arrhythmias that the arrhythmia detector 262 can detect include, but are not limited to, SVT (e.g., AF), VT and VF. As mentioned above, a tachycardia is a fast heart rate (usually over 100 beats per minute) typically caused by disease or injury. It can also be part of a normal response to increased activity or oxygen demands. The average heart beats between 60 and 100 times per minute. When the tachycardia is due to disease or injury, it usually requires treatment. Tachycardias may begin in the upper chambers of the heart (the atria) or the lower chambers of the heart (the ventricles). VTs begins in the ventricles. Some are harmless, but others are life threatening in that they can quickly deteriorate to VF. Some VTs are harmful even before they deteriorate into VF, or even if they don't deteriorate to VF (e.g., they can cause hemodynamic deterioration that can cause collapse).

VF is a very fast (e.g., over 200 beats per minute) and chaotic heart rate in the lower chambers of the heart, resulting from multiple areas of the ventricles attempting to control the heart's rhythm. VF can occur spontaneously (generally caused by heart disease) or when VT has persisted too long. When the ventricles fibrillate, they do not contract normally, so they cannot effectively pump blood. The instant VF begins, effective blood pumping stops. VF typically quickly becomes more erratic, often resulting in sudden cardiac arrest. This arrhythmia should be corrected immediately via a shock from an external defibrillator or an implantable cardioverter defibrillator (ICD). The defibrillator stops the chaotic electrical activity and restores normal heart rhythm. These are just a few examples of the types of arrhythmias that the arrhythmia detector 262 can detect. One of ordinary skill in the art will appreciate that other types of arrhythmias can be detected, and information for such other types of arrhythmias can be stored.

In accordance with embodiments of the present invention, the implantable device 110 can store, in memory 294, IEGM data corresponding to the period immediately prior to, during and subsequent to a detected arrhythmia. The implantable device can also store data that identifies the type of arrhythmia, the time of the arrhythmia (e.g., a time stamp), the duration of the arrhythmia, as well as any other type of information that a caregiver may deem useful. U.S. Pat. No. 4,295,474 (Fischell) and U.S. Pat. No. 5,732,708 (Nau et al.), each of which is incorporated herein by reference, provide exemplary additional details of the types of data that can be stored in response to the detection of an arrhythmia (and other cardiac events), and how such data can be efficiently and effectively stored.

Still referring to FIG. 2, cardiac signals are also applied to the inputs of an analog-to-digital (ND) data acquisition system 290. The data acquisition system 290 is configured to acquire intracardiac electrogram (IEGM) signals, convert the raw analog data into a digital signal, and store the digital signals for later processing and/or telemetric transmission to an external device 202. The data acquisition system 290 is coupled to the right atrial lead 120, the coronary sinus lead 124, and the right ventricular lead 130 through the switch 274 to sample cardiac signals across any pair of desired electrodes. In specific embodiments, the data acquisition system 290 may be used to acquire IEGM signals for the analysis.

The data acquisition system 290 can be coupled to the microcontroller 260, or other detection circuitry, for detecting an evoked response from the heart 112 in response to an applied stimulus, thereby aiding in the detection of "capture". Capture occurs when an electrical stimulus applied to the heart is of sufficient energy to depolarize the cardiac tissue, thereby causing the heart muscle to contract. The microcontroller 260 detects a depolarization signal during a window following a stimulation pulse, the presence of which indicates that capture has occurred. The microcontroller 260 enables capture detection by triggering the ventricular pulse generator 272 to generate a stimulation pulse, starting a capture detection window using the timing control circuitry 279 within the microcontroller 260, and enabling the data acquisition system 290 via control signal 292 to sample the cardiac signal that falls in the capture detection window and, based on the amplitude, determines if capture has occurred.

The implementation of capture detection circuitry and algorithms are well known. See for example, U.S. Pat. No. 4,729,376 (Decote, Jr.); U.S. Pat. No. 4,708,142 (Decote, Jr.); U.S. Pat. No. 4,686,988 (Sholder); U.S. Pat. No. 4,969,467 (Callaghan et. al.); and U.S. Pat. No. 5,350,410 (Mann et. al.), which patents are hereby incorporated herein by reference. The type of capture detection system used is not critical to the present invention.

The microcontroller 260 is further coupled to the memory 294 by a suitable data/address bus 296, wherein the programmable operating parameters used by the microcontroller 260 are stored and modified, as required, in order to customize the operation of the implantable device 110 to suit the needs of a particular patient. Such operating parameters define, for example, pacing pulse amplitude, pulse duration, electrode polarity, rate, sensitivity, automatic features, arrhythmia detection criteria, and the amplitude, waveshape and vector of each shocking pulse to be delivered to the patient's heart 112 within each respective tier of therapy.

The operating parameters of the implantable device 110, including arrhythmia discrimination parameters, may be non-invasively programmed into the memory 294 through a telemetry circuit 201 in telemetric communication with an external device 202, such as a programmer, transtelephonic transceiver, or a diagnostic system analyzer. The telemetry circuit 201 can be activated by the microcontroller 260 by a control signal 206. The telemetry circuit 201 advantageously allows intracardiac electrograms and status information relating to the operation of the device 110 (as contained in the microcontroller 260 or memory 294) to be sent to the external device 202 through an established communication link 204. For examples of such devices, see U.S. Pat. No. 4,809,697, entitled "Interactive Programming and Diagnostic System for use with Implantable Pacemaker" (Causey, III et al.); U.S. Pat. No. 4,944,299, entitled "High Speed Digital Telemetry System for Implantable Device" (Silvian); and U.S. Pat. No. 6,275,734 entitled "Efficient Generation of Sensing Signals in an Implantable Medical Device such as a Pacemaker or ICD" (McClure et al.), which patents are hereby incorporated herein by reference.

The implantable device 110 additionally includes a battery 211 which provides operating power to all of the circuits shown in FIG. 2. If the implantable device 110 also employs shocking therapy, the battery 211 should be capable of operating at low current drains for long periods of time, and then be capable of providing high-current pulses (for capacitor charging) when the patient requires a shock pulse. The battery 211 should also have a predictable discharge characteristic so that elective replacement time can be detected. Certain embodiments of the present invention, as will be appreciated from the discussion further below, can be used to extend the life a the battery 211 by reducing the quantity of high voltage shocks delivered.

The implantable device 110 can also include a magnet detection circuitry (not shown), coupled to the microcontroller 260. It is the purpose of the magnet detection circuitry to detect when a magnet is placed over the implantable device 110, which magnet may be used by a clinician to perform various test functions of the implantable device 110 and/or to signal the microcontroller 260 that the external programmer 202 is in place to receive or transmit data to the microcontroller 260 through the telemetry circuits 201.

As further shown in FIG. 2, the device 110 is also shown as having an impedance measuring circuit 213 which is enabled by the microcontroller 260 via a control signal 214. The known uses for an impedance measuring circuit 213 include, but are not limited to, lead impedance surveillance during the acute and chronic phases for proper lead positioning or dislodgement; detecting operable electrodes and automatically switching to an operable pair if dislodgement occurs; measuring respiration or minute ventilation; measuring thoracic impedance for determining shock thresholds and heart failure condition; detecting when the device has been implanted; measuring stroke volume; and detecting the opening of heart valves, etc. The impedance measuring circuit 213 is advantageously coupled to the switch 274 so that any desired electrode may be used. The impedance measuring circuit 213 is not critical to the present invention and is shown only for completeness.

Because the implantable device 110 may operate as an implantable cardioverter defibrillator device, it should detect the occurrence of an arrhythmia, and automatically apply an appropriate electrical shock therapy to the heart aimed at terminating the detected arrhythmia. To this end, the microcontroller 260 further controls a shocking circuit 216 by way of a control signal 218. The shocking circuit 216 generates shocking pulses of low (up to 0.5 Joules), moderate (0.5-10 Joules), or high energy (11 to 40 Joules), as controlled by the microcontroller 260. Such shocking pulses are applied to the patient's heart 112 through at least two shocking electrodes, and as shown in this embodiment, selected from the left atrial coil electrode 228, the RV coil electrode 236, and/or the SVC coil electrode 238. As noted above, the housing 240 may act as an active electrode in combination with the RV electrode 236, or as part of a split electrical vector using the SVC coil electrode 238 or the left atrial coil electrode 228 (i.e., using the RV electrode as a common electrode). Use of additional and/or alternative electrodes is also possible, as would be appreciated by one of ordinary skill in the art.

The above described implantable device 110 was described as an exemplary device. One or ordinary skill in the art would understand that embodiments of the present invention can be used with alternative types of implantable devices. Accordingly, embodiments of the present invention should not be limited to use only with the above described device.

Exemplary External Programmer

Figure 3A:
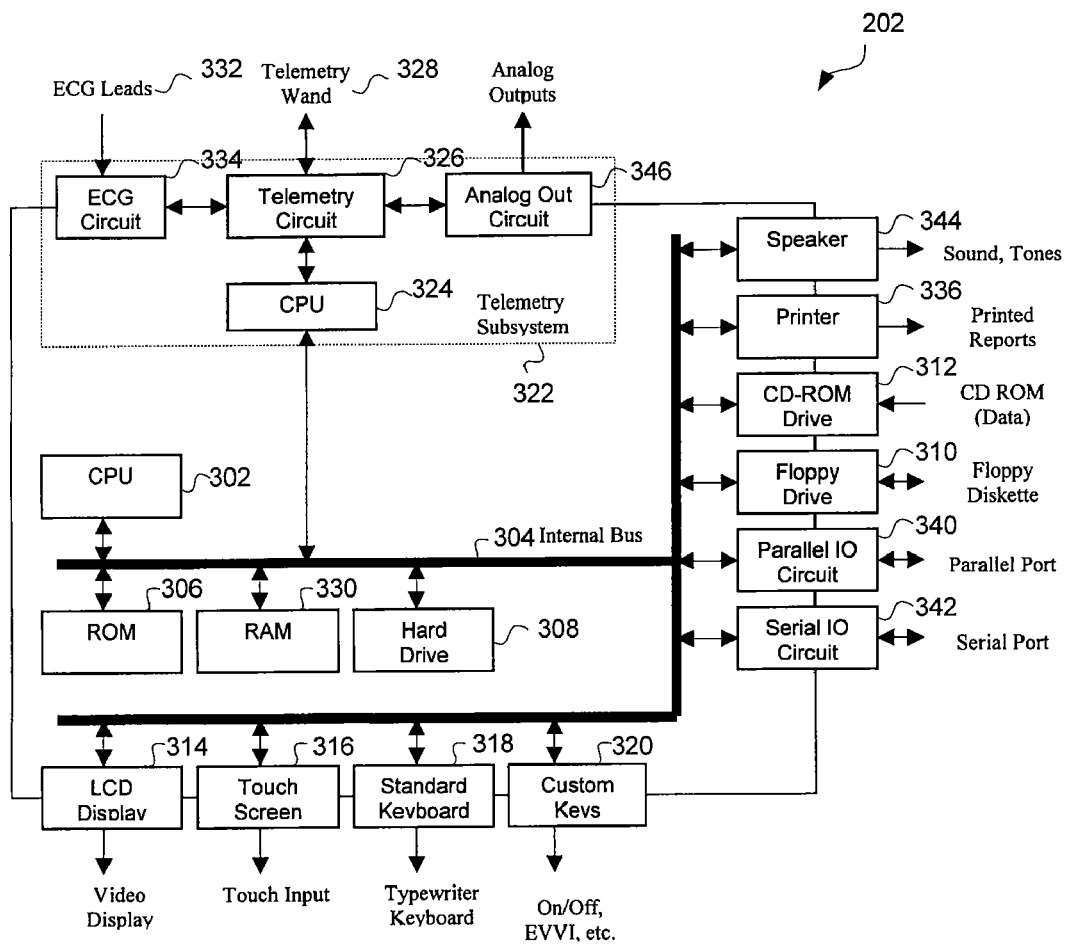
FIG. 3A is a functional block diagram of an exemplary external programmer device that can be used to program the implantable device of FIGS. 1 and 2, and to upload and analyze data collected by the implantable device.

FIG. 3A will now be used to illustrate components of an exemplary external programmer 202 for use in programming the implantable device 110, uploading data from the implantable device, and analyzing such data. Briefly, the programmer permits a physician or other caregiver to program the operation of the implantable device 110 and to retrieve and display information received from the implantable device such as IEGM data and device diagnostic data. Additionally, the external programmer can receive and display EKG data from separate external EKG leads that may be attached to the patient. As will be described in further detail below, in accordance with embodiments of the present invention, the external programmer 202 is capable of processing and analyzing data received from the implantable device 110.

Operations of the programmer 202 are controlled by a CPU 302, which may be a generally programmable microprocessor or microcontroller or may be a dedicated processing device such as an application specific integrated circuit (ASIC) or the like. Software instructions to be performed by the CPU are accessed via an internal bus 304 from a read only memory (ROM) 306 and random access memory 330. Additional software may be accessed from a hard drive 308, floppy drive 310, and CD ROM drive 312, or other suitable permanent mass storage device. Depending upon the specific implementation, a basic input output system (BIOS) is retrieved from the ROM by CPU at power up. Based upon instructions provided in the BIOS, the CPU "boots up" the overall system in accordance with well-established computer processing techniques.

Once operating, the CPU 302 displays a menu of programming options to the user via an LCD display 314 or other suitable computer display device. To this end, the CPU may, for example, display a menu of specific programming parameters of the implantable device to be programmed or may display a menu of types of diagnostic data to be retrieved and displayed. In response thereto, the caregiver enters various commands via either a touch screen 316 overlaid on the LCD display or through a standard keyboard 318 supplemented by additional custom keys 320, such as an emergency VVI (EVVI) key. The EVVI key sets the implantable device to a safe WI mode with high pacing outputs. This ensures life sustaining pacing operation in nearly all situations but by no means is it desirable to leave the implantable device in the EVVI mode at all times. These are just a few examples of the types of user interfaces of the programmer, which are not meant to be limiting. Inclusion and use of other types of user interfaces are possible, and within the scope of the present invention.

Once all pacing leads are mounted and the implantable device 110 is implanted, the various devices are programmed. Typically, the caregiver initially controls the programmer 202 to retrieve data stored within any implantable device 110 and to also retrieve EKG data from EKG leads 332, if any, coupled to the patient. To this end, the CPU 302 transmits appropriate signals to a telemetry subsystem 322, which provides components for directly interfacing with the implantable device 110, and the EKG leads. Telemetry subsystem 322 includes its own separate CPU 324 for coordinating the operations of the telemetry subsystem. Main CPU 302 of programmer communicates with telemetry subsystem CPU 324 via internal bus 304. Telemetry subsystem 322 additionally includes a telemetry circuit 326 connected to telemetry wand 328, which, in turn, receives and transmits signals electromagnetically from the telemetry unit 201 of the implantable device 110. The telemetry wand 328 is placed over the chest of the patient near the implantable device to permit reliable transmission of data between the telemetry wand 328 and the implantable device 110.

Typically, at the beginning of the programming session, the external programming device 202 controls the implantable device 110 via appropriate signals generated by the telemetry wand 328 to output all previously recorded patient and device diagnostic information. Patient diagnostic information includes, for example, recorded IEGM data and statistical patient data such as the percentage of paced versus sensed heartbeats. Device diagnostic data includes, for example, information representative of the operation of the implantable device such as lead impedances, battery voltages, battery recommended replacement time (RRT) information and the like. Data retrieved from the implantable device 110 is stored by external programmer 202, e.g., within a random access memory (RAM) 330, hard drive 308 or within a floppy diskette placed within floppy drive 310. Additionally, or in the alternative, data may be permanently or semi-permanently stored within a compact disk (CD) or other digital media disk, if the overall system is configured with a drive for recording data onto digital media disks, such as a write once read many (WORM) drive.

Once all patient and device diagnostic data previously stored within the implantable device 110 is transferred to programmer 202, the implantable device 110 may be further controlled to transmit additional data in real time as it is detected by the implantable device 110, such as additional IEGM data, lead impedance data, and the like.

As will be explained in more detail below, in specific embodiments of the present invention the programmer 202, the programmer can be used to adjust the values and or uses of discriminator parameters that the device 110 uses to discriminate between VT and SVT. More specifically, the telemetry subsystem 322 can be used to make such adjustments to the discriminator parameters of the implantable device 110, as will be described in more detail below.

It is also possible that the telemetry subsystem 322 receives EKG signals from EKG leads 332 via an EKG processing circuit 334. As with data retrieved from the implantable device itself, signals received from the EKG leads can be stored within one or more of the storage devices of the external programmer. Typically, EKG leads output analog electrical signals representative of the EKG. Accordingly, EKG circuit 334 includes analog to digital conversion circuitry for converting the signals to digital data appropriate for further processing within programmer. Depending upon the implementation, the EKG circuit 334 may be configured to convert the analog signals into event record data for ease of processing along with the event record data retrieved from the implantable device. Typically, signals received from the EKG leads are received and processed in real time. Thus, the programmer 202 can receive data both from the implantable device 110 and from the external EKG leads 332.

Data retrieved from the implantable device 110 includes parameters representative of the current programming state of the implantable device 110. Under the control of the caregiver, the external programmer 202 displays the current programming parameters and permits the caregiver to reprogram the parameters. To this end, the caregiver enters appropriate commands via any of the aforementioned input devices and, under control of CPU 302, the programming commands are converted to specific programming parameters for transmission to the implantable device 110 via telemetry wand 328 to thereby reprogram the implantable device 110. A wide variety of parameters may be programmed by the caregiver, including, but not limited to atrioventricular and inter-ventricular delay values. As mentioned above, programmable parameters also include those parameters that can be used to discriminate between different types of arrhythmias. Prior to reprogramming specific parameters, the caregiver may control the external programmer 202 to display any or all of the data retrieved from the implantable device 110 or from the EKG leads, including displays of ECGs, IEGMs, and statistical patient information. Any or all of the information displayed by programmer may also be printed using a printer 336.

The programmer 202 can also include a modem (not shown) to permit direct transmission of data to other programmers via the public switched telephone network (PSTN) or other interconnection line, such as a T1 line or fiber optic cable. Depending upon the implementation, the modem may be connected directly to internal bus 304 may be connected to the internal bus via either a parallel port 340 or a serial port 342. Other peripheral devices may be connected to the external programmer via parallel port 340 or a serial port 342 as well. Although one of each is shown, a plurality of input output (IO) ports might be provided. A speaker 344 is included for providing audible tones to the user, such as a warning beep in the event improper input is provided by the caregiver. The telemetry subsystem 322 additionally includes an analog output circuit 346 for controlling the transmission of analog output signals, such as IEGM signals output to an EKG machine or chart recorder.

With the programmer 202 configured as shown, a physician or other caregiver operating the external programmer 202 is capable of retrieving, processing and displaying a wide range of information received from the EKG leads or from the implantable device 110 and to initially program and/or to reprogram the implantable device 110 if needed. The descriptions provided herein with respect to FIG. 3A are intended merely to provide an overview of the operation of an exemplary external programmer 202 and are not intended to describe in detail every feature of the hardware and software of the device and is not intended to provide an exhaustive list of the functions performed by the device.

Figure 3B:
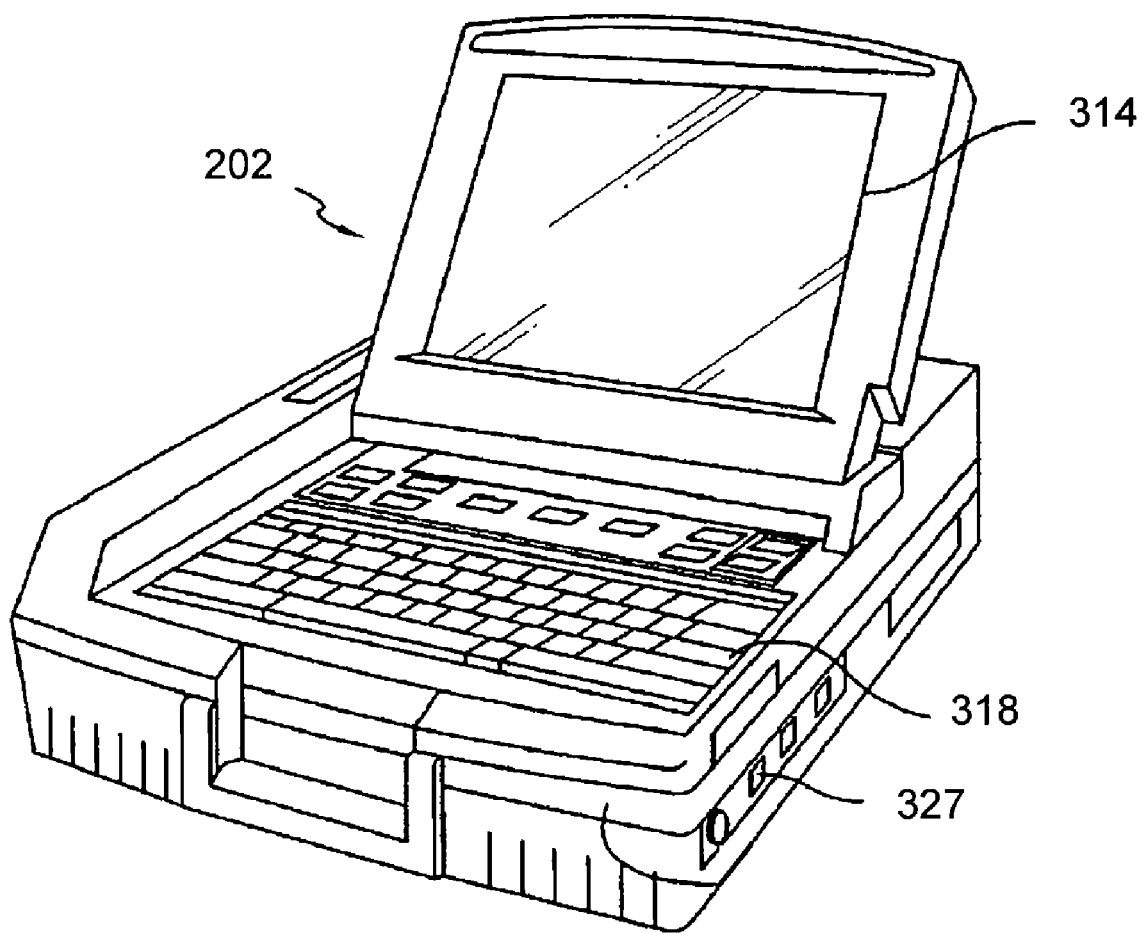
FIG. 3B is an exemplary perspective view of the exemplary external programmer device of FIG. 3A.

FIG. 3B is an exemplary perspective view of the exemplary programmer 202 introduced in FIG. 3A. Referring to FIG. 3B, the programmer 202 is shown as including a display 314, a keyboard 318, and a connector 327 for accepting a cable of a telemetry wand (328 in FIG. 3A).

Specific Embodiments of the Present Invention

Programming of discrimination parameters today generally consists of a simple "discriminators on/off" control and/or the ability to individually fine-tune values of parameters such as sudden onset, interval stability, morphology discrimination, AV association threshold, etc. More specifically, the values of individual parameters can be fine-tuned, and the combination and relationship of the various parameters can be altered. For example, in order for the device to characterize a rhythm as VT, the user can choose to allow either morphology or interval stability criteria to be met; alternatively, the user could specify that both morphology and interval stability criteria must be met. The more stringent the requirements (e.g., the more criteria are logically "AND-ed" together, the tighter the interval stability parameter is set, etc.), the higher the specificity of the algorithm. A high specificity can avoid delivery of inappropriate VT therapies in response to SVTs, but may result in a lower sensitivity. The converse is also true: the higher the sensitivity of the algorithm, typically the lower the specificity.

As used herein, sensitivity refers to the likelihood that an episode of VT will actually be characterized as VT; and specificity refers to the likelihood that only episodes of VT (as opposed to episodes of SVT) will actually be characterized as VT. For example, a device can have a 100% specificity and an 80% specificity if it always characterizes episodes of VT as VT, but also characterizes some episodes of SVT as VT. For another example, a device can have an 80% sensitivity and a 100% specificity if it never mischaracterizes episodes of SVT as VT, but misses detecting some episodes of VT. Also, as used herein, the terms "an episode of VT" and simply "VT" are generally used interchangeably, as are the terms "an episode of SVT" and simply "SVT". In other words, it is the same to say that "an actual episode of VT is characterized as an episode of VT" as it is to say "an actual VT is characterized as VT" or "an actual episode of VT is characterized as VT".

Often, the subtleties of discriminator parameter programming, and the implications of such programming's effects on sensitivity and specificity are lost on caregivers (also referred to as users). As a result, caregivers typically leave the discrimination parameters and criteria at their default settings unless the patient either receives inappropriate therapies or has appropriate therapies withheld. This must be considered suboptimal practice, since inappropriate behavior must be exhibited (with potential clinical consequences for the patient) before the parameters are adjusted. In a practical sense, the caregiver is typically skilled at judging the relative risks and benefits to an individual patient of different combinations of sensitivity and specificity, but not at how to achieve that individualized optimal balance by programming.

In accordance with embodiments of the present invention, the settings of discriminators are driven by a caregiver's choice of balance of sensitivity and specificity, rather than by requiring the caregiver to choose specific discriminator settings. This allows the caregiver to program according to desired clinical outcomes and/or indications, rather than according to device-specific criteria.

In specific embodiments, there are, in essence, two defaults options presented to a caregiver, including a "primary prevention" option and a "secondary prevention" option. The primary prevention option is for use with primary prevention patients, for whom the caregiver's primary goal is to prevent sudden death yet avoid inappropriate therapies, even if that were to result in occasionally missing slower VTs unless/until they accelerated/degenerated to VF. The use of this option would result in a high specificity, with a somewhat lower sensitivity. On the other hand, the secondary prevention option is for use with patients with known arrhythmias, where the clinician's goal is to be sure to treat every episode of VT, even if this were to result in occasional inappropriate therapy deliveries (e.g., treating SVT using VT therapy). The use of this option would result in a high sensitivity, with a somewhat lower specificity.

Instead of having the two choices presented to caregiver labeled "primary prevention" and "secondary prevention", the two choices presented to the caregiver can be labeled, e.g., "High Specificity/Lower Sensitivity" and "High Sensitivity/Lower Specificity". The latter set of labels would be more descriptive of the results of the clinician's choice, while the former would be more descriptive of the clinical application of the device for the patient. In alternative embodiments, more than two choices are provided to the clinician, allowing for various degrees of balance between sensitivity and specificity. In any of the embodiments described above, the "low" and "high" sensitivity and specificity nomenclature could be replaced with sensitivity and specificity numbers.

In yet other embodiments, the clinician is presented with a continuum of choices. For example, the programmer could present the clinician with a sliding bar scale, with one extreme being high sensitivity/lower specificity and the other being lower sensitivity/high specificity, and a continuum of options in between. The slide bar can be manipulated (e.g., slid) using a physical slide bar. There can also be a representation of a slide bar visible on a display of the external programmer, and the user can use a mouse, joystick, keyboard, trackball, wheel, touch screen, or other user interface, to manipulate the slide bar.

Regardless of which of the above embodiments is implemented, the selection of a sensitivity/specificity balance or similar indication would automatically result in adjustment of the individual parameters "under the hood" to achieve the desired clinical result. In this manner, the clinician is thinking and programming in clinical terms, and the ICD system (programmer and device) is adjusting device behavior accordingly. The option for the clinician to further fine-tune parameters in the more traditional sense could be preserved, if further adjustment(s) is/are needed.

Figure 4:
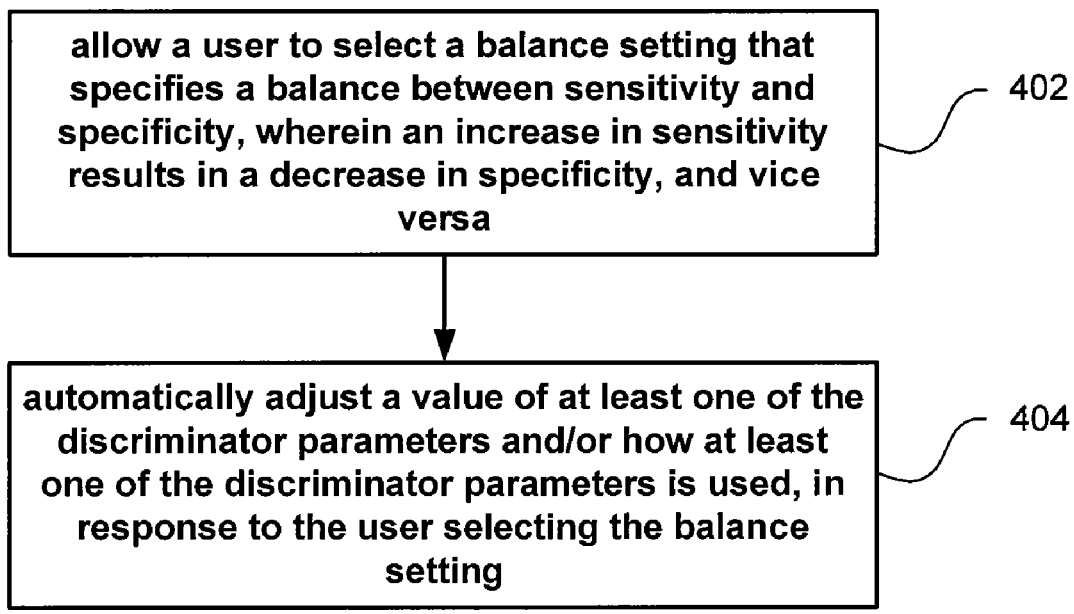
FIG. 4 is a high level flow diagram that is used to summarize specific embodiments of the present invention.

Specific embodiments of the present invention shall now be summarized with reference to the high level flow diagram of FIG. 4. Such embodiments are for use with an implantable cardiac device that has discriminator parameters that the device uses to discriminate between ventricular tachycardia (VT) and supraventricular tachyarrhythmia (SVT). Referring to FIG. 4, at a step 402, a user is allowed to select a balance setting that specifies a balance between sensitivity and specificity, wherein an increase in sensitivity results in a decrease in specificity, and vice versa. Still referring to FIG. 4, at a step 404, a value of at least one of the discriminator parameters and/or how at least one of the discriminator parameters is used, is automatically adjusted, in response to the user selecting the balance setting. In such embodiments, the more the balance setting favors sensitivity, then the more likely an actual VT will be characterized as VT, but the more likely an actual SVT may be characterized as VT. Conversely, the more the balance setting favors specificity, then the less likely an actual SVT will characterized as VT, but the less likely an actual VT may be characterizes as VT.

Embodiments of the present invention can include obtaining an intracardiac electrogram (IEGM), and monitoring the IEGM to detect arrhythmias, where the values and uses of the discriminator parameters, as adjusted in response to the user selecting the balance setting, are used to discriminate between VT and SVT. Exemplary leads and electrodes that can be used to obtain an IEGM were discussed above with reference to FIGS. 1 and 2. It is well know how to obtain an IEGM, thus additional details of how to obtain an IEGM are not necessary. Further, it is well known that an implantable cardiac device (e.g., 110) can use discriminator parameters to discriminate between VT and SVT. Nevertheless, some additional details of how this can be done are provide below. What is not known are steps 402 and 404. Accordingly, additional details of these steps are provided below. Further, it is not known that the values and uses of discriminator parameters, which are used for classifying an arrhythmia, can be automatically adjusted in response to a user selecting a balance setting between sensitivity and specificity.

In accordance with specific embodiments, step 404 can involve automatically adjusting the value of one or more (and likely two or more) discriminator parameter(s). Exemplary discriminators parameters include, but are not limited to, a tachycardia detection rate parameter, an interval stability parameter, a sudden onset parameter, and a morphology parameter. Each of these discriminator parameters are explained below. The value of each discriminator parameter can either be increased or decreased to change a balance between sensitivity and specificity. Whether a value needs to be increased or decreased to increase sensitivity (and decrease specificity) depends on the specific parameter, and can also depends on how the parameter is used in an algorithm.

Alternatively, or additionally, step 404 can involve adjusting whether a discriminator parameter is used or not, e.g., adjusting whether the discriminator criteria that uses the discriminator parameter is turned on or off. For example, if an interval stability criteria is turned on, then the interval stability parameter value is used in an algorithm to assist in classifying an arrhythmia as VT or SVT. In contrast, if the interval stability criteria is turned off, then the interval stability parameter value is not used in an algorithm for such classification of an arrhythmia. Such criteria can be, e.g., a branch of an algorithm, which can be turned on or off.

Additionally, or alternatively, step 404 can involve adjusting how many discriminator criteria must be satisfied for a rhythm to be characterized as VT. For example, this can include adjusting the number N, where N out of M different criteria must be satisfied for a rhythm to be characterized as VT. For example, a relatively high sensitivity and low specificity can be achieved if only one of four discriminator criteria needs to be satisfied for an arrhythmia to be classified as VT. A relatively lower sensitivity and higher specificity can be achieved, e.g., if all four discriminator criteria need to be satisfied for an arrhythmia to be classified as VT. Additionally, or alternatively, step 404 can involve adjusting whether discriminator criteria are "AND-ed" or "OR-ed" in an algorithm. Typically, the more criteria are "AND-ed", the higher the specificity. These are just a few examples of how value and uses of discriminator parameters can be adjusted. One of ordinary skill in the art reading this description will understand that there are other possible adjustments that can be made that are also within the scope of the present invention.

As explained above, such adjustments are automatically performed, in response to the user adjusting the balance setting between sensitivity and specificity. In specific embodiments, this means that an external programmer and/or implantable cardiac device will make such adjustments in response to a caregiver simply selecting (e.g., changing, or initially selecting) a balance setting, without the caregiver necessarily knowing which parameter values are being adjusted, or how uses of parameters are being adjusted. This is analogous to a person listening to a stereo changing the stereo's setting from "classical" to "jazz", and the stereo automatically adjusting the bass, treble and balance levels of the stereo, in response to the selected setting (e.g., classical or jazz), without the person necessarily knowing which levels are being adjusted, and how such levels are adjusted.

Figure 5:
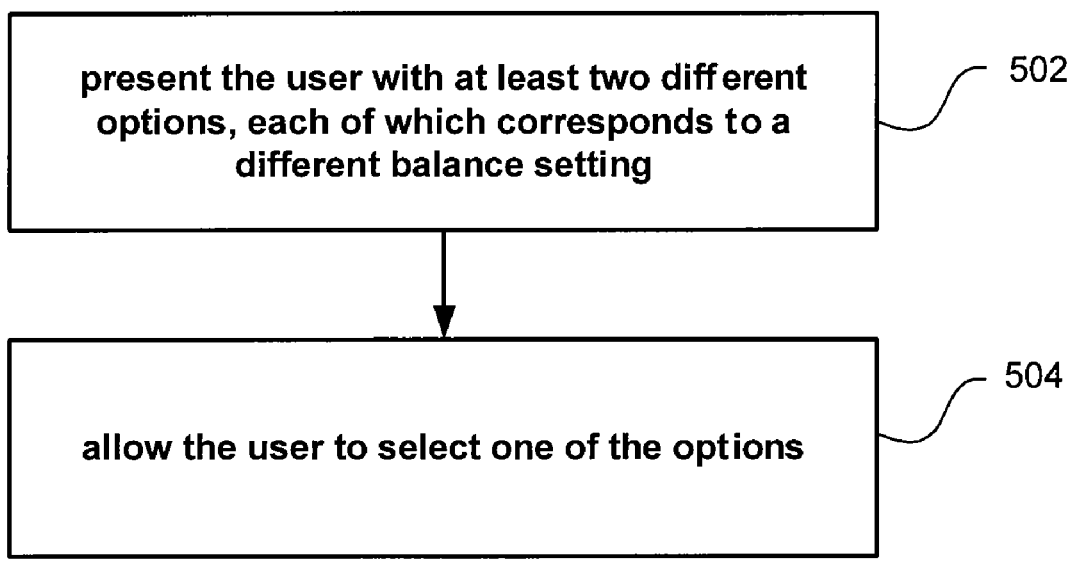
FIG. 5 is a high level flow diagram that is used to explain additional details of one of the steps of the flow diagram of FIG. 4, according to specific embodiments of the present invention.

Additional details of step 402 are described with reference to the high level flow diagram of FIG. 5. Referring to FIG. 5, at a step 502, the user is presented with at least two different options, each of which corresponds to a different balance setting. For example, the at least two different options can include a first option and a second option, where the first option corresponds to a first sensitivity and first specificity, and the second option corresponding to a second sensitivity and a second specificity, with the first sensitivity being greater than the second sensitivity, and the first specificity being less than the second specificity. For a more specific example, the first option may correspond to a 97% sensitivity and a 80% specificity; and the second option may correspond to a 92% sensitivity a 88% specificity. In specific embodiments a first option can be presented to the user as a "secondary prevention" option, and a second option can be presented to the user as a "primary prevention" option. More than two options are possible, and likely.

Still referring to FIG. 5, at step 504, the user is allowed to select one of the at least two different options. The user is likely a caregiver, which as discussed above, can be a physician, clinician, specialist, nurse, but is not limited thereto. Such options can be selected, e.g., by pressing corresponding physical buttons or the like on an external programmer (e.g., 202) that is in wireless communications with an implantable cardiac device (e.g., 110). In other words, step 504 can include accepting an input from a user via physical buttons, or the like. Alternatively, the various balance options can be presented to the user at step 502 via a display (e.g., 316), which can be a touch screen type display (e.g., 318), of the programmer (e.g., 202). The user can then be allowed to select one of the options using a user interface, such as a keyboard, touch screen, mouse, joystick, etc., to select the desired balance.

Figure 6A:
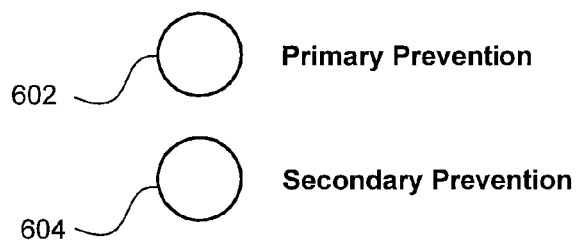
FIGS. 6A and 6B illustrate examples of balance setting options that can be presented to a user, in one of the steps of FIG. 5.

FIG. 6A illustrates that the options presented to a user can include a "primary prevention" option 602 and a "secondary prevention" option 604. In response to a user selecting the "primary prevention" option 602, value(s) and/or use(s) of discriminator parameter(s) are automatically adjusted to those that have been programmed into the implantable device and/or external programmer for use with primary prevention patients, where the primary goal is to prevent sudden death yet avoid inappropriate therapies, even if they were to result in occasionally missing slower VTs unless/until they accelerated/degenerated to VF. Such parameters would result in a relatively high specificity, with a somewhat lower sensitivity, as mentioned above.

In response to a user selecting the "secondary prevention" option 604, value(s) and/or uses(s) of discriminator parameter(s) are automatically adjusted to those that have been programmed into the implantable device and/or external programmer for use with secondary prevention patients, whom have known arrhythmias, where the goal is to be sure to treat every episode of VT, even if this were to result in occasional inappropriate therapy deliveries. Such parameters would result in a relatively high sensitivity, with a somewhat lower specificity, as mentioned above.

Figure 6B:
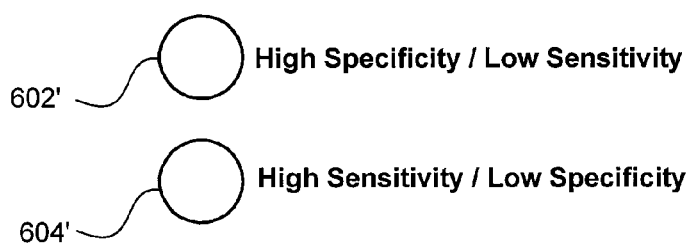

Instead of presenting the options to the user as "primary prevention" and "secondary prevention" options 602 and 604, the options presented to the user can include a "high specificity/low sensitivity" option 602' and a "high sensitivity/low specificity" option 604', as shown in FIG. 6B. The discriminator parameters that correspond to the "primary prevention" option 602 can be the same as the discriminator parameters that correspond to the "high specificity/low sensitivity" option 602', but that need not be the case. Similarly, the discriminator parameters that correspond to the "secondary prevention" option 604 can be the same as the discriminator parameters that correspond to the "high sensitivity/low specificity" option 604', but that need not be the case. Note that the use of the terms "high" and "low" are relative terms. For example, it may be that a sensitivity of 98% is high, and that a sensitivity of 80% is low. Similarly, a specificity of 80% can be low, and a specificity of 88% can be high.

Figure 6C:
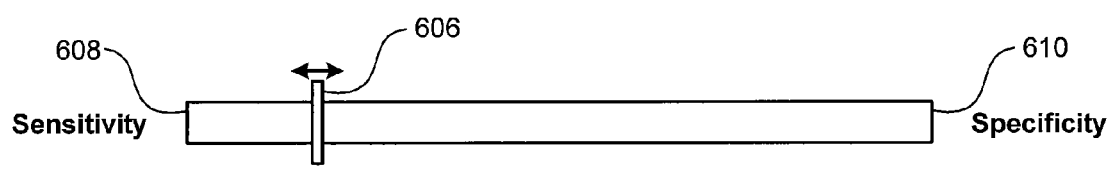
FIG. 6C is used to illustrate still another way in which balance setting options can be presented to a user, and how such options can be selected.

In FIGS. 6A and 6B, two options are shown as being presented to a caregiver. In specific embodiments, more than two options can be presented to the user, as mentioned above. For example, three options can be presented to the user, where the middle option has a relatively more even balance between sensitivity and specificity. Even more granularity of options is also possible, and likely. Referring to FIG. 6C, in specific embodiments a sliding scale bar 606 having a first end 608 and a second end 610, can be presented to a user, where the first end 608 corresponds to a first sensitivity and a first specificity, and the second end 610 corresponds to a second sensitivity and a second specificity (where the first sensitivity is higher than the second sensitivity, and the first specificity is lower than the second specificity). The sliding scale bar 606 can be a physical user interface of the programmer, but is more likely a graphical representation shown on a display or touch screen. Accordingly, the bar 606 of the sliding scale can be moved physically (if it's a physical bar), or using keys (e.g., arrow keys) of a keyboard, using a mouse, joystick, or the like, touching a touch screen, etc. In such embodiments, the user can select a position on the scale between, and inclusive of, the first and second ends 608 and 610, wherein the selected position corresponds to the balance setting selected by the user.

As explained above, once a user selects a balance option, e.g., using an external programmer, at least one discriminator parameter (and likely multiple discriminator parameters) of the implantable cardiac device are automatically adjusted. This can be accomplished in various different manners. In certain embodiments, the external programmer determines the values and/or uses of discriminator parameters that correspond to the user selected balance, and the external programmer transmits such parameter values and/or instructions for uses of parameters to the implantable cardiac device (so that the cardiac device's discriminator parameter values and/or uses are appropriately adjusted). In alternative embodiments, the external programmer transmits the user selected balance setting to the implantable cardiac device, the implantable cardiac device determines the discriminator parameter values and/or uses that correspond to the received balance setting, and the implantable cardiac device adjusts its parameters accordingly. Either way, the values and/or uses of discriminator parameters are automatically adjusted in response to a user selected balance setting that specifies a balance between sensitivity and specificity.

As mentioned above, exemplary discriminator parameters whose values or uses can be adjusted include a tachycardia detection rate parameter, an interval stability parameter, a sudden onset parameter, and a morphology parameter. Each of these exemplary parameters shall now be briefly discussed.

A tachycardia rate detection parameter can define the ventricular rate threshold above which a ventricular rate will be classified as a tachyarrhythmia. If no other discrimination criteria are turned on, the device will classify any rhythm with a ventricular rate above the tachycardia detection rate (but below the VF detection threshold) as a VT. This will result in a high sensitivity, but a relatively low specificity, because many SVTs may be classified as VT. In order to increase the specificity, which typically results in some reduction in sensitivity, additional discriminator criteria can be turned on, and "AND-ed" with the tachycardia detection rate discriminator criteria. A balance between sensitivity and specificity can also be adjusted by adjusting the value of the tachycardia detection rate discriminator parameter, with a lower such value typically resulting in an increase in sensitivity and a decrease in specificity, and vice verse.

An interval stability parameter can be used to discriminate between episodes of VT and episodes of AF, because VTs are typically very stable, whereas the rhythm from one beat to the next during AF is typically less stable (i.e., more irregular). Depending upon the algorithm used, the value of an interval stability parameter can be a value of stability (also referred to as variability), which can be defined by a range, variance, standard deviation, or the like. For example, a cardiac rhythm exceeds the tachycardia detection rate parameter, and the stability is within that defined by the stability discriminator value (e.g., the standard deviation of the rhythm is less than the standard deviation discriminator value), then the arrhythmia will be classified as VT. Interval stability is sometime referred to as rate stability, because rate and interval are simply inverses of one another.

A sudden onset discriminator parameter can help distinguish between VT and a sinus tachycardia type SVT that is due to exercise (e.g., walking up a flight of stairs). Typically, a sinus tachycardia has a gradual rate of onset, while VT has a more abrupt onset. Such onset can be measured, e.g., by determining a difference between the average RR interval for N beats prior to a first beat that exceeds the tachycardia detection rate, and the average RR interval for N beats following the first beat that exceeds the tachycardia detection rate (e.g., N can be 1 or more). Accordingly, the value of a sudden onset discriminator parameter can be specified in milliseconds. Where the sudden onset discriminator value is exceeded, the implantable cardiac device interprets that as an indicator of VT. Where a sudden onset discriminator value is not exceeded, the implantable cardiac device interprets that as an indicator of SVT. Accordingly, the lower the magnitude of the sudden onset discriminator value, the greater the sensitivity, but the lower the specificity. Conversely, the greater the magnitude of the sudden onset discriminator value, the lower the sensitivity, but the higher the specificity. This is just one example of a sudden onset discriminator criteria, which is not meant to be limiting.

Where both a tachycardia detection rate criteria and a sudden onset criteria are turned on (i.e., when both a tachycardia detection rate parameter and a sudden onset parameter are used), it can be that both have to be satisfied for an arrhythmia to be classified as VT. For example, if the tachycardia detection rate parameter is exceeded, but the sudden onset parameter is not exceeded, then a tachycardia may be classified as SVT. While a sudden onset discriminator parameter can be used to discriminate VT from sinus tachycardia, it can not necessarily help distinguish from other types of SVTs. As just explained above, interval stability discriminator parameter can be used to discriminate VT from AF, which conducts irregularity to the ventricles, but not necessarily discriminate from other SVTs.

To further increase sensitivity, a morphology discriminator parameter can be used (i.e., a morphology discriminator criteria can be turned on). SVTs originate in the atria and follow the normal conduction pathway to the ventricles (typically via the AV node), causing the morphology (shape) of the resulting QRS complexes to look similar to the morphology of a QRS complex of a normal sinus rhythm. In contrast, VT arises from outside normal conduction system, causing the morphology of the resulting QRS complex to be less similar to that of a normal sinus rhythm. To perform such morphology comparisons, a template QRS complex is typically obtained and stored when a patient is known to have a normal sinus rhythm. Thereafter, the template QRS complex can be compared to present QRS complexes in real or near real time, to determine a level of similarity. A morphology discriminator parameter can specify, e.g., the level of similarity below which a rhythm is classified as indicative of VT, and above which the rhythm is classified as indicative of SVT. For a more specific example, a morphology algorithm can measure attributes such as the number of peaks, amplitude of peaks, polarity, and area under curves of a QRS complex, and compares such complexes to the template QRS complex to generate a percent match between 0 and 100%. For this example, the morphology discriminator parameter can specify the percentage match, above which a complex is classified as indicative of SVT, and below which the complex is classified as indicative of VT.

Provided above are just a few examples of discriminator parameters/criteria that can be automatically adjusted using embodiments of the present invention. Automatic adjustments of alternative and additional parameters/criteria are also within the scope of the present invention, including, but not limited to, rate branch discriminators. For example, embodiments of the present invention can be used to automatically turn on or off a rate branch algorithm, or to adjust parameters used in such an algorithm, or to turn on or off specific branches of such an algorithm.

The present invention has been described above with the aid of functional building blocks illustrating the performance of specified functions and relationships thereof. The boundaries of these functional building blocks have often been arbitrarily defined herein for the convenience of the description. Alternate boundaries can be defined so long as the specified functions and relationships thereof are appropriately performed. Any such alternate boundaries are thus within the scope and spirit of the claimed invention. For example, it would be possible to combine or separate some of the steps shown in FIGS. without substantially changing the overall events and results.

The previous description of the preferred embodiments is provided to enable any person skilled in the art to make or use the embodiments of the present invention. While the invention has been particularly shown and described with reference to preferred embodiments thereof, it will be understood by those skilled in the art that various changes in form and details may be made therein without departing from the spirit and scope of the invention.

What is claimed is:

1. A method for use with an implantable cardiac device that has discriminator parameters that the device uses to discriminate between ventricular tachycardia (VT) and supraventricular tachyarrhythmia (SVT), the method comprising:
    allowing a user to select a balance setting that specifies a balance between sensitivity and specificity, wherein an increase in sensitivity results in a decrease in specificity, and vice versa; and
    automatically adjusting a value of at least one of the discriminator parameters and/or how at least one of the discriminator parameters is used, in response to the user selecting the balance setting, wherein the at least one discriminator parameters that is automatically adjusted does not comprise the balance setting;
    wherein the more the balance setting favors sensitivity, then the more likely an actual VT will be characterized as VT, but the more likely an actual SVT may be characterized as VT; and
    wherein the more the balance setting favors specificity, then the less likely an actual SVT will characterized as VT, but the less likely an actual VT may be characterizes as VT.

2. The method of claim 1, further comprising presenting the user with at least two different default options, each of which corresponds to a different balance setting, wherein the allowing step comprises allowing the user to select one of the options, wherein the at least two different options includes at least a first option and a second option, the first option corresponding to a first sensitivity and first specificity, and the second option corresponding to a second sensitivity and a second specificity, where the first sensitivity is greater than the second sensitivity, and the first specificity is less than the second specificity.

3. The method of claim 2, wherein:
    the first option is presented to the user as a secondary prevention option; and
    the second option is presented to the user as a primary prevention option.

4. The method of claim 2, wherein;
    the presenting step includes presenting the user with the at least two different options via a programmer configured to wirelessly communicate with the implantable cardiac stimulation device; and
    the allowing step includes allowing the user to select one of the at least two different options, using a user interface of the programmer.

5. The method of claim 4, wherein:
the presenting step includes presenting the user with a sliding scale bar having a first end and a second end, the first end corresponding to a first sensitivity and first specificity, and the second end corresponding to a second sensitivity and a second specificity, where the first sensitivity is greater than the second sensitivity, and the first specificity is less than the second specificity; and
the allowing step includes allowing the user to select a position on the scale between, and inclusive of, the first and second ends, wherein the selected position corresponds to the balance setting selected by the user.

6. The method of claim 1, wherein the discriminator parameters include at least one of the following:
a tachycardia detection rate parameter;
an interval stability parameter;
a sudden onset parameter; and
a morphology parameter.

7. The method of claim 1, wherein the automatically adjusting step includes adjusting a value of at least one of the discriminator parameters, in response to the user selecting the balance setting.

8. The method of claim 1, wherein the automatically adjusting step includes adjusting a value of at least one of the following discriminator parameters, in response to the user selecting the balance setting:
a tachycardia detection rate parameter;
an interval stability parameter;
an atrioventricular association parameter;
a sudden onset parameter; and
a morphology parameter.

9. The method of claim 1, wherein the automatically adjusting step includes adjusting a value of at least two of the following discriminator parameters, in response to the user selecting the balance setting:
a tachycardia detection rate parameter;
an interval stability parameter;
an atrioventricular association parameter;
a sudden onset parameter; and
a morphology parameter.

10. The method of claim 1, wherein the automatically adjusting step includes adjusting how many discriminator criteria must be satisfied for a rhythm to be characterized as VT, where at least some of the discriminator criteria are specified at least in part by a corresponding one of the discriminator parameters.

11. The method of claim 1, wherein the automatically adjusting includes adjusting which discriminator criteria are turned on, where at least some of the discriminator criteria are specified at least in part by a corresponding one of the discriminator parameters.

12. The method of claim 1, further comprising:
obtaining an intracardiac electrogram (IEGM); and
monitoring the IEGM to detect arrhythmias, wherein the values and uses of the discriminator parameters, as adjusted in response to the user selecting the balance setting, are used to discriminate between VT and SVT.

13. A method for use with a programmer and an implantable cardiac device, where the programmer is configured to wirelessly communicate with the implantable cardiac device, and where the implantable cardiac device has discriminator parameters that the device uses to discriminate between ventricular tachycardia (VT) and supraventricular tachyarrhythmia (SVT), the method comprising:
presenting a user with the at least two different default options via the programmer;
allowing the user to select one of the at least two different options, using a user interface of the programmer;
automatically adjusting a value of at least one the discriminator parameters and/or how at least one of the discriminator parameters is used, in response to the user selecting the one of the options, wherein the at least one discriminator parameters that is automatically adjusted is not the selected option;
wherein each option specifies a different balance between sensitivity and specificity;
wherein the greater the sensitivity, then the more likely an actual VT will be characterized as VT, but the more likely an actual SVT may be characterized as VT; and
wherein the greater the specificity, then the less likely an actual VT will be characterizes as VT, but the less likely an actual SVT may characterized as VT.

14. The method of claim 13, wherein the automatically adjusting step includes:
determining, within the programmer, changes to a value of at least one the discriminator parameters and/or how at least one of the discriminator parameters is used, in response to the user selecting one of the options; and
transmitting said changes from the programmer to the implantable device.

15. The method of claim 13, wherein the automatically adjusting step includes:
transmitting the selected option, from the programmer to the implantable device, in response to the user selecting one of the options; and
determining, within the implantable device, changes to a value of at least one the discriminator parameters and/or how at least one of the discriminator parameters is used based on the selected option.

16. The method of claim 13, wherein;
the presenting step comprises presenting the user with the at least three different options via the programmer; and
the allowing step comprises allowing the user to select one of the at least three different options, using the user interface of the programmer.

17. The method of claim 13, wherein the presenting step includes:
presenting the user with at least a secondary prevention option and a primary prevention option;
the secondary prevention option having a first sensitivity and a first specificity;
the primary prevention option having a second sensitivity and a second specificity;
the first sensitivity being greater than the second sensitivity; and
the second specificity being greater than the first specificity.

18. The method of claim 13, further comprising:
obtaining an intracardiac electrogram (IEGM); and
monitoring the IEGM to detect arrhythmias, wherein the values and uses of the discriminator parameters, as adjusted in response to the user selecting one of the options, are used to discriminate between VT and SVT.

19. A programmer, comprising:
a transmitter to wirelessly communicate with an implantable cardiac device that has discriminator parameters that the device uses to discriminate between ventricular tachycardia (VT) and supraventricular tachyarrhythmia (SVT);
a display to present a user with at least two different options, wherein each option specifies a different balance between sensitivity and specificity;

a user interface to allow the user to select one of the at least two different options; and a processor programmed to determine changes to a value of at least one of the discriminator parameters and/or how at least one of the discriminator parameters is used, in response to the user selecting one of the options, wherein the at least one discriminator parameters is not the balance setting; and wherein the transmitter is also to transmit said changes to the implantable cardiac device;

wherein the greater the sensitivity, then the more likely an actual VT will be characterized as VT, but the more likely an actual SVT may be characterized as VT; and wherein the greater the specificity, then the less likely an actual VT will be characterizes as VT, but the less likely an actual SVT may characterized as VT.

20. The programmer of claim 19, wherein the display presents the user with at least a secondary prevention option and primary prevention option.

* * * * *